(12) United States Patent
Akhlaghi et al.

(10) Patent No.: US 10,126,316 B2
(45) Date of Patent: Nov. 13, 2018

(54) SYSTEMS AND METHODS FOR THE MEASUREMENT OF TACROLIMUS IN ORAL FLUIDS BY LIQUID CHROMATOGRAPHY TANDEM MASS SPECTROMETRY

(71) Applicant: Rhode Island Council on Postsecondary Education, Statutory Board of Education, and Rhode Island Board of Governors for Higher Education, Warwick, RI (US)

(72) Inventors: Fatemeh Akhlaghi, Wakerfield, RI (US); Mwlod Ghareeb, Kingston, RI (US)

(73) Assignee: Rhode Island Council on Postsecondary Education, Statutory Sucessor to the Rhode Island Board of Education, and Rhode Island Board of Governors for Higher Education, Kingston, RI (US)

(*) Notice: Subject to any disclaimer, the term of this patent is extended or adjusted under 35 U.S.C. 154(b) by 9 days.

(21) Appl. No.: 15/466,467

(22) Filed: Mar. 22, 2017

(65) Prior Publication Data

US 2017/0276693 A1 Sep. 28, 2017

Related U.S. Application Data

(60) Provisional application No. 62/311,667, filed on Mar. 22, 2016.

(51) Int. Cl.
*B01D 15/14* (2006.01)
*B01D 15/22* (2006.01)
(Continued)

(52) U.S. Cl.
CPC ......... *G01N 33/9493* (2013.01); *B01D 15/14* (2013.01); *B01D 15/22* (2013.01);
(Continued)

(58) Field of Classification Search
CPC ...... B01D 15/14; B01D 15/22; B01D 15/426; G01N 2560/00; G01N 33/9493;
(Continued)

(56) References Cited

U.S. PATENT DOCUMENTS

2013/0265054 A1* 10/2013 Lowery, Jr. .......... G01R 33/281
324/319
2014/0158881 A1* 6/2014 Cooper .............. G01N 30/8665
250/282

* cited by examiner

Primary Examiner — Jennifer Wecker
(74) Attorney, Agent, or Firm — Davis, Brown, Koehn, Shors & Roberts, P.C.; Sean D. Solberg

(57) ABSTRACT

Disclosed is a method of measuring tacrolimus levels in a subject. In exemplary embodiments, the method comprises the steps of: collecting oral fluid from the subject; homogenizing the oral fluid; combining the homogenized oral fluid with a precipitating solvent; separating oral fluid components on a liquid chromatography column by gradient elution with a mixture of a solvent A and a solvent B, wherein the solvent A is about 2 mM ammonium acetate/0.1% (v/v) formic acid in water and solvent B is about 2 mM ammonium acetate/0.1% (v/v) formic acid in MeOH and wherein the amount of solvent B is increased from about 50% (v/v) to about 98% (v/v); and quantifying the amount of tacrolimus in the oral fluid by mass spectrometry.

20 Claims, 9 Drawing Sheets

(51) Int. Cl.
*B01D 15/42* (2006.01)
*G01N 30/00* (2006.01)
*G01N 30/02* (2006.01)
*G01N 33/94* (2006.01)
*G06F 19/00* (2018.01)
*G01N 30/04* (2006.01)

(52) U.S. Cl.
CPC ........... *B01D 15/426* (2013.01); *G01N 30/00* (2013.01); *G06F 19/00* (2013.01); *G06F 19/3456* (2013.01); *G01N 2030/022* (2013.01); *G01N 2030/027* (2013.01); *G01N 2030/042* (2013.01); *G01N 2030/045* (2013.01); *G01N 2560/00* (2013.01)

(58) Field of Classification Search
CPC ............. G01N 30/00; G01N 2030/022; G01N 2030/027; G01N 2030/042; G01N 2030/045; G06F 19/3456
See application file for complete search history.

SYSTEMS AND METHODS FOR THE MEASUREMENT OF TACROLIMUS IN ORAL FLUIDS BY LIQUID CHROMATOGRAPHY TANDEM MASS SPECTROMETRY

CROSS-REFERENCE TO RELATED APPLICATION(S)

This application claims priority to U.S. Provisional Application No. 62/311,667 filed Mar. 22, 2016 and entitled "Systems and Methods for the Measurement of Tacrolimus in Oral Fluids by Liquid Chromatography Tandem Mass Spectrometry," which is hereby incorporated by reference in its entirety under 35 U.S.C. § 119(e).

BACKGROUND

Tacrolimus (TAC) is a widely prescribed immunosuppressive agent for solid organ transplantation to prevent allograft loss. It inhibits activation and proliferation of CD4+ and CD8+T-lymphocytes by binding to immunophilin FK506-binding protein (FKBP12) as well as inhibiting calcineurin phosphatase and subsequent IL-2 production. TAC is highly lipophilic and is excreted from the body following metabolism by the CYP450 3A4/5 enzymes. Due to genetic polymorphisms in the drug metabolizing enzyme CYP3A, bioavailability of TAC can vary significantly among individuals. In addition, TAC is a substrate for the P-glycoprotein efflux transporter (Pgp), also known as multidrug resistance protein 1 (MDR1), a cell membrane ATP-dependent efflux pump encoded by the ABCB1 gene with broad substrate specificity. Differences in the expression level of MDR1 and ABCB1 may also contribute to inter-individual variability of TAC bioavailability. As a result of its narrow therapeutic index and high variability in bioavailability, ongoing monitoring of TAC is essential for maintaining optimal therapeutic concentrations to ensure allograft survival and reduce nephrotoxicity.

TAC concentrations in peripheral blood mononuclear cells (PBMCs) and biopsy from implanted tissues have shown to be good indicators for therapeutic efficacy and predictors for allograft rejection in liver and kidney transplant recipients. Because of the invasiveness of biopsy and complicated sample preparation procedures, the use of these specimens in routine TDM is not practical. TAC blood levels have been shown to have poor correlation with, in situ levels, in lymphocytes and tissues as well as with unbound fractions. As a result, whole blood sampling fails to provide a reliable prediction of allograft status and toxicity. Accordingly, there is a need in the art for a less invasive method that provides reliable prediction of allograft status and total exposure to free/pharmacologically active form of TAC.

BRIEF SUMMARY

Described herein are various embodiments relating to devices, systems and methods for measurement of tacrolimus in oral fluids of a subject, using liquid chromatography tandem mass spectrometry (LC-MS/MS). In certain aspects, the method comprises collecting oral fluid from the subject; homogenizing the oral fluid; combining the homogenized oral fluid with a precipitating solvent; separating oral fluid components on a liquid chromatography column by gradient elution with a mixture of a solvent A and a solvent B, wherein the solvent A is about 2 mM ammonium acetate/0.1% (v/v) formic acid in water, and solvent B is about 2 mM ammonium acetate/0.1% (v/v) formic acid in MeOH, and wherein the amount of solvent B is increased from about 50% (v/v) to about 98% (v/v); and determining amount of tacrolimus in the oral fluid by mass spectrometry.

Further disclosed herein is method of adjusting tacrolimus dosage for an organ transplant patient. According to certain embodiments, the method includes the steps of collecting an oral fluid sample from the patient; homogenizing the oral fluid; combining the homogenized oral fluid with a precipitating solvent; and separating oral fluid components on a liquid chromatography column by gradient elution with a mixture of a solvent A and a solvent B, wherein the solvent A is about 2 mM ammonium acetate/0.1% (v/v) formic acid in water and solvent B is about 2 mM ammonium acetate/0.1% (v/v) formic acid in MeOH and wherein the amount of solvent B is increased from about 50% (v/v) to about 98% (v/v); and determining the concentration of tacrolimus in the oral fluid by mass spectrometry; wherein an oral fluid concentration of tacrolimus above 200 ng/L indicates a need to decrease tacrolimus dosage and an oral fluid concentration of tacrolimus below 5 ng/L indicates a need to increase tacrolimus dosage.

Further disclosed herein is a kit for measuring tacrolimus in a subject that according to certain embodiments comprises: a vessel for collecting oral fluid from the subject; a homogenization buffer comprising a precipitating solvent; one or more liquid chromatography columns; a first elution buffer comprising about 2 mM ammonium acetate/0.1% (v/v) formic acid in water; a second elution buffer comprising about 2 mM ammonium acetate/0.1% (v/v) formic acid in MeOH; and an internal standard sample.

While multiple embodiments are disclosed, still other embodiments of the disclosure will become apparent to those skilled in the art from the following detailed description, which shows and describes illustrative embodiments of the disclosed, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

DETAILED DESCRIPTION

As used above, and throughout the description of the invention, the following abbreviations, unless otherwise indicated, shall be understood to have the following meanings:
ACN—Acetonitrile;
ASC—Ascomycin;
CV—Coefficient of variation;
ESI—Electrospray ionization;
IS—Internal standard;
ISR—Incurred Sample Reanalysis;
LC-MS/MS—Liquid chromatography tandem mass spectrometry;
LLOQ—Lower limit of quantification;
ME—Matrix effect;
MeOH—Methanol;
MRM—Multiple reaction monitoring;
MS—Mass spectrometry;
MW—Molecular Weight;
OF—Oral fluid;
QCs—Quality controls;
RTR—Renal transplant recipients;
S/N—Signal to noise ratio;
TAC—Tacrolimus;
TDM—Therapeutic Drug Monitoring Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "Internal standard" means a chemical substance that is added in a constant amount to samples, blank and calibration standards in an analysis. This chemical substance is used for calibration by plotting the ratio of the analyte signal to the internal standard signal as a function of the analyte concentration of the standards. This is done to measure and correct for the loss of analyte during sample preparation or sample inlet. Particularly, the internal standard is a compound that has similar, but not same, chemical structure to the analyte.

"Tacrolimus," also referred to herein as (TAC) means a compound having the chemical structure:

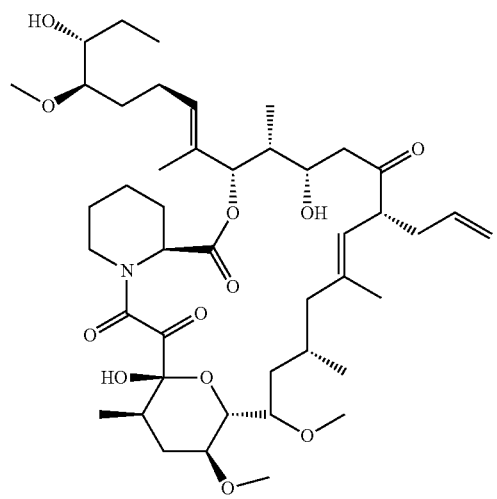

Tacrolimus is also known as also FK-506, fujimycin, or the trade names Prograf, Advagraf, and Protopic.

Figure 1:
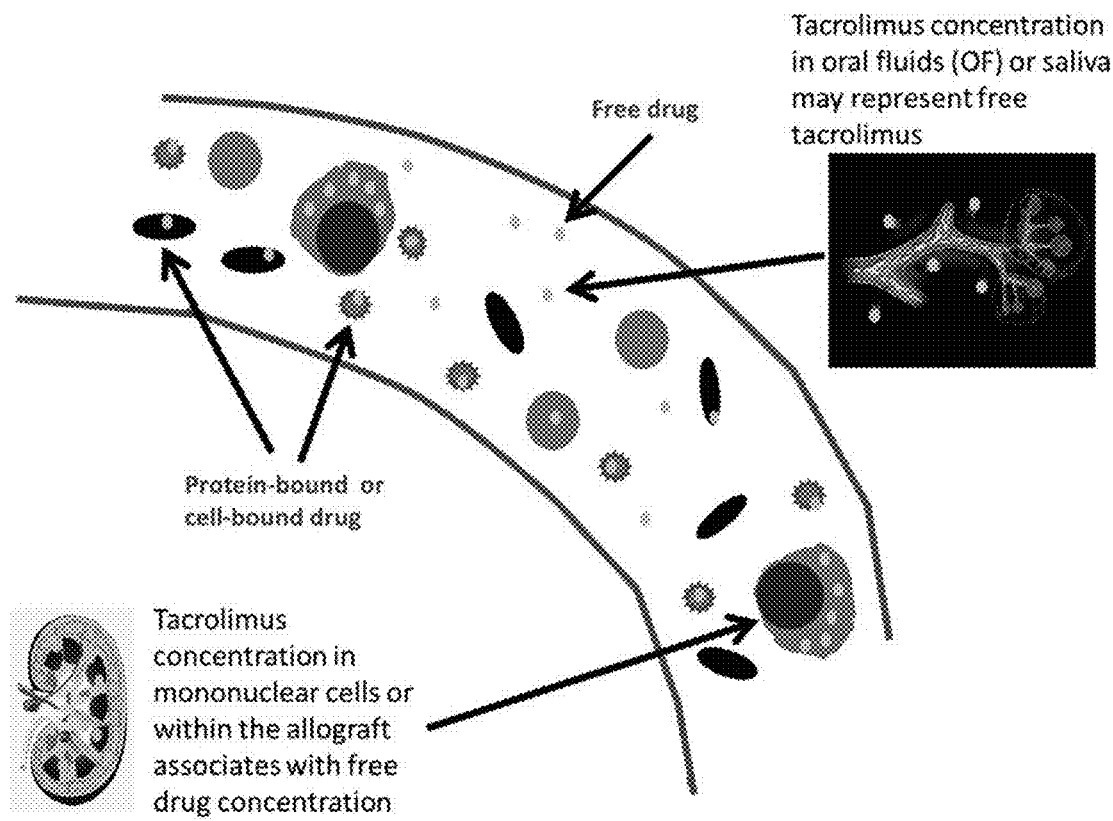
FIG. 1 shows a schematic diagram illustrating the impact of free drug penetration on allograft tissue and the relationship between free drug concentration with drug concentration in oral fluids (Saliva).

Only 1% of total concentration of TAC in blood is present as free or pharmacologically active form. As shown schematically in FIG. 1, free drug can penetrate into allograft and shows higher correlation with organ rejection. For example, the free fraction of another immunosuppressive agent cyclosporine was associated to a greater extent with the incidence of heart transplant rejection than total concentration of cyclosporine. Similarly, the free concentration of TAC in blood or plasma is significantly lower in patients experiencing liver allograft rejection than in other patients, whereas the concentration of total TAC is not different. Therefore, monitoring free TAC concentration instead of total concentration provides a closer approximation to clinical outcomes.

Disclosed herein is a method for measuring tacrolimus in a subject. In certain aspects, the method comprises collecting oral fluid from the subject; homogenizing the oral fluid; combining the homogenized oral fluid with a precipitating solvent; separating oral fluid components on a liquid chromatography column by gradient elution with a mixture of a solvent A and a solvent B; and determining amount of tacrolimus in the oral fluid by mass spectrometry. According to certain aspects, solvent A is comprised of ammonium acetate and formic acid in water, and solvent B is comprised of ammonium acetate and formic acid in MeOH. In further aspects, solvent A is about 2 mM ammonium acetate/0.1% (v/v) formic acid in water, and solvent B is about 2 mM ammonium acetate/0.1% (v/v) formic acid in MeOH. In yet further aspects, the amount of solvent B is increased from about 50% (v/v) to about 98% (v/v). In certain aspects, solvent B is increased from about 50% (v/v) to about 98% (v/v) over period of about 30 seconds. In further aspects, solvent B is maintained at about 98% (v/v) for about 1.8 minutes. According to still further aspects, the method further comprises utilizing an internal standard. In certain embodiments, the internal standard is ascomycin, which is an ethyl analog of tacrolimus.

In certain aspects, the precipitating solvent used in the disclosed method is acetonitrile. The ratio of precipitating solvents may vary according to certain embodiments. In certain embodiments, the volume of acetonitrile is about double the volume of oral fluid.

In certain aspects, mass spectrometry is performed in multiple reaction monitoring (MRM) mode. In further aspects, mass spectrometry is performed wherein the collision energy is 20, cone voltage is 28, capillary voltage is 1.50 kV, source temperature is 150° C., cone gas flow is 25 L/hr, desolvation gas flow is 1000 L/hr, and collision gas flow is 0.15 mL/min. According to still further aspects, precursors are [M+NH4]+. One skilled in the art will appreciate that other precursors are possible.

In certain embodiments, the liquid chromatography column has a particle size of about 1.7 μm and a pore size of about 130 Å. In certain exemplary embodiments, the liquid chromatography column is an Acquity® UPLC BEH C18 (2.1 mm×50 mm) column. In further embodiments a precolumn is utilized. In exemplary embodiments, the precolumn is an Acquity UPLC BEH C18, (2.1 mm×5 mm) pre-column with 1.7 μm particle size and 130 Å porosity.

In certain aspects, the subject has received an organ transplant. In further aspects, the organ transplant is a liver or a kidney or a heart transplant.

Also disclosed herein, is a method of adjusting tacrolimus dosage for an organ transplant patient. According to certain exemplary embodiments of these methods, adjusting tacrolimus dosage for an organ transplant patient involves collecting an oral fluid sample from the patient; homogenizing the oral fluid; combining the homogenized oral fluid with a precipitating solvent; and analyzing the oral fluid mixture with a LC-MS/MS system. In certain embodiments, analyzing the oral fluid is accomplished by separating oral fluid components on a liquid chromatography column by the methods disclosed herein. In exemplary embodiments, analyzing the oral fluid is accomplished by separating oral fluid components on a liquid chromatography column by gradient elution with a mixture of a solvent A and a solvent B. In certain aspects, the solvent A is about 2 mM ammonium acetate/0.1% (v/v) formic acid in water and solvent B is about 2 mM ammonium acetate/0.1% (v/v) formic acid in MeOH and wherein the amount of solvent B is increased from about 50% (v/v) to about 98% (v/v); and determining the concentration of tacrolimus in the oral fluid by mass spectrometry; wherein a concentration of tacrolimus above a certain predefined threshold indicates a need to decrease the dosage of tacrolimus delivered to the patient and dosage below a certain predefined threshold indicates a need to increase tacrolimus dosage delivered to the patient. According to certain exemplary embodiments, an oral fluid concentration of tacrolimus above 200 ng/L indicates a need to decrease tacrolimus and an oral fluid concentration of tacrolimus below 5 ng/L indicates a need to increase tacrolimus dosage.

Also disclosed herein is a kit for measuring tacrolimus in a subject. According to certain embodiments, the kit comprises a vessel for collecting oral fluid from the subject; a homogenization buffer comprising a precipitating solvent; one or more liquid chromatography columns; a first elution buffer comprised of ammonium acetate and formic acid in water, and second elution buffer comprised of ammonium acetate and formic acid in MeOH; and an internal standard sample. According to certain embodiments, the first elution buffer comprises about 2 mM ammonium acetate/0.1% (v/v) formic acid in water and the second elution buffer comprises about 2 mM ammonium acetate/0.1% (v/v) formic acid in MeOH. In certain embodiments, the internal standard is ascomycin.

EXAMPLES

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Example 1

Chemicals and Reagents

Tacrolimus ($C_{44}H_{69}NO_{12}$, MW=804.02, 1.0 mg/mL solution in acetonitrile) and the internal standard (IS) ascomycin (ASC, $C_{43}H_{69}NO_{12}$, MW=792.01, 1.0 mg/mL solution in acetonitrile) were purchased from Cerilliant Corporation (Round Rock, Tex., USA). Acetonitrile (ACN) (Optima LC/MS), ammonium acetate (Crystalline/HPLC), formic acid (Optima LC/MS), and methanol (MeOH) (Optima LC/MS) were purchased from Fisher Scientific (Fair Lawn, N.J., USA). Deionized water was obtained from Milli-Q Synthesis system fitted with Q-Gard 2 Purification Pack (Millipore, Bedford, Mass., USA). AquaSil Siliconizing Fluid was purchased from Thermo Fisher Scientific Inc. (Franklin, Mass., USA). Drug-free human OF from six donors was obtained from Bioreclamation Inc. (Westbury, N.Y., USA).

Apparatus

Samples were sonicated using Branson® Sonicator (Danbury, Conn., USA) to produce a homogeneous mixture. Supernatant was obtained using Eppendorf 5810 centrifuge from Micro and Nanotechnology (Urbana, Ill., USA). Samples were analyzed using liquid chromatography tandem mass spectrometry (LC-MS/MS). The LC-MS/MS system consisted of Acquity UPLC from Waters Corp. (Milford, Mass., USA) connected to a Xevo TQ MS mass spectrometer from Waters Corp. (Milford, Mass., USA). MassLynx™ (V 4.1) was used to control the system and data acquisition, and data was processed using TargetLynx™. The UPLC system had binary pump and was equipped with built in column heater. A twenty microliter sample loop was used to deliver 10 μL of the sample in partial loop mode. Blood contamination of OF samples was assessed using an ELISA method utilizing a SpectraMax M5e Microplate Reader (Sunnyvale, Calif., USA).

Chromatographic Conditions

An Acquity UPLC BEH C18 (2.1×50 mm) column with 1.7 μm-particle size and 130 Å pores size (Waters Corp) was used for chromatographic separation. An Acquity UPLC BEH C18, (2.1×5 mm) VanGuard pre-column with 1.7 µm particle size and 130 Å porosity (Waters Corp) was connected immediately to the inlet of the analytical column. The temperature of the column was kept at 60° C. and the auto-sampler temperature was maintained at 20° C.

The chromatographic conditions were optimized and the gradient elution described here provided the best separation of TAC and IS from suppressing phospholipid ions. Chromatographic separation was achieved using a mobile phase which consisted of water containing 2 mM ammonium acetate/0.1% (v/v) formic acid (solvent A); and MeOH containing 2 mM ammonium acetate/0.1% (v/v) formic acid (solvent B). The mobile phase was delivered at 0.4 mL/min flow rate. The run cycle started at 50% solvent (B) and increased gradually to 98% over 0.5 min and was maintained at this level until 1.8 min. To re-equilibrate the column for the next run, solvent (B) decreased within 0.1 min to 50% and remained at 50% until the end of the run at 2.2 minutes. The diversion valve was set to deliver the first 0.70 min and from 1.20 min until the end of each run to waste. The elution time of TAC and IS was 1.0 min.

Mass Spectrometry Conditions

Mass spectrometry detection and quantification of TAC and ASC was performed in positive electrospray ionization (ESI) and multiple reaction monitoring (MRM) modes. Intellistart tool was used to obtain initial mass spectrometry parameters in low mass resolution analysis mode followed by manual tuning to achieve highest possible sensitivity. Final mass spectrometry parameters were as following: collision energy (CE)=22 and 20 for ASC and TAC respectively, cone voltage (CV)=28, capillary voltage (kV)=1.50, source temperature (° C.)=150, cone gas flow (L/hr)=25, desolvation gas flow (L/hr)=1000, and collision gas flow (mL/min)=0.15. Ammonium adducts $[M+NH_4]^+$ were selected as precursors for MRM with transitions (m/z, Q1→Q3) of (m/z, 809.30→756.30) and (m/z, 821.30→768.35) for ASC and TAC, respectively.

Standards, Quality Controls, and Internal Standard Solutions Preparation

Sub-stock and working stock solutions of ASC and TAC were prepared from the original stock (1 mg/mL) using ACN and MeOH, respectively, and stored at −20° C. Standards and quality controls (QCs) were prepared by spiking the OF with serially diluted working stock solutions (<5% of total OF volume) to achieve desired concentrations. A final concentration of 400 pg/mL ASC solution in ACN was used as precipitating solvent.

Patients Samples

Study protocols were approved by Institutional Review Board at Rhode Island Hospital (Providence, R.I.). After giving informed consent, kidney transplant recipients attending kidney transplant clinics were recruited. All patients were on triple immunosuppressive regimen including tacrolimus, prednisone, and mycophenolic acid or azathioprine. In two studies, patients were asked to give venous blood samples (about 4 mL collected with ethylenediaminetetraacetic acid as anti-coagulant) and matching OF samples. The OF samples were collected by passive drool into siliconized plastic cups. All blood and OF samples were kept on ice until transferred to the Biomedical and Pharmaceutical Sciences (BPS) department at University of Rhode Island and stored at −80° C. until analyzed.

Sample Extraction

Calibration standards, quality controls (QCs), blank, and patients' OF samples were allowed to thaw at room temperature. After vortexing for 5 seconds, the samples were sonicated for 5-10 seconds (depending on samples volume) to breakdown salivary components and to produce a homogenous mixture. This is a crucial step that will ensure adequate recovery of TAC from OF. A 50 µL aliquot of homogenized OF sample was transferred into a 1.5 mL polypropylene tube and 100 µL of precipitating solvent was added (IS final concentration was 400 pg/mL). After vortexing for 10 seconds, samples were centrifuged at 10,000 g for 5 min at 20° C. The supernatant was then transferred into an auto-sampler vial and 10 µL was injected onto the column.

Statistical Data Analysis

Statistical analysis was performed using the SPSS software (version 19.0, SPSS Inc., Chicago, Ill., USA) and GraphPad Prism (version 4.0, GraphPad Software, Inc., La Jolla, Calif., USA). Normal distribution of the data was checked graphically and confirmed with the Shapiro-Wilk test.

Assay Validation

Standards and QCs

The method was validated in accordance with current version of FDA guidance for industry bioanalytical method validation. Tacrolimus to IS peak ratio against tacrolimus nominal concentration was used to construct the calibration curve and fitted using (1/x) weighting method. Calibration curve points were, 10, 20, 50, 100, 250, 750, 1440, and 1600 pg/mL. Concentration of quality controls were set at 30, 200, and 1200 pg/mL. To determine accuracy and precision of the assay, three different batches of OF were spiked with the working stock solution to achieve standards and QCs (six replicates) concentrations and extracted as described in sample extraction section.

Sensitivity and Selectivity

Lower limit of quantification (LLOQ) was determined as the concentration that had signal to noise ratio (S/N) of at least 10, accuracy between 80-120%, and coefficient of variation (CV) less than 20%. Acceptance criteria for QCs was accuracy between 85-115% and CV less than 15%. Selectivity assessed by inspecting the presence of noise or peaks in chromatograms represent blank OF samples injections (from 6 donors) compared with LLOQ sample chromatogram.

Stability

Stability studies were performed by measuring TAC concentrations in QC1 and QC3, in three replicates. Freeze and thaw (after three freeze and thaw cycles), bench-top, auto-sampler (by re-injecting one of validation batch after it was left in the auto-sampler for 24 h and 48 h), and short-term stability up to one month were investigated.

Matrix Effect and Recovery

The presence and possible influence of matrix effect (ME) in OF was studied in two different ways. First, chromatograms were obtained from the post-column infusion test. This test involved continuous infusion of 98% methanol (which represents the composition of mobile phase at elution time of ASC and TAC) containing 1 ng/mL of ASC and TAC at 20 µL/min flow rate after the column through a Tee connection. After establishing the baseline, a 10 µL of blank extracted OF sample was injected by HPLC. The obtained chromatogram was then checked for signs of ion suppression and/or enhancement in comparison to blank injection of neat solution (1:2, water:ACN). Second, the possible interference of OF components, namely the phospholipids, was studied. To do so, MRM transitions of abundant phospholipids were added to MS method to enable us to visually locate their elution region of these phospholipids.

The influence of increasing ratio of precipitating solvents on the ME was also studied to select the ratio that offers the cleanest chromatography trace. Two different sets of QC1 and QC3 samples were prepared, in triplicate, either by 1) QCs samples (set 1) prepared by adding ACN to OF samples spiked with TAC as prescribed in sample extraction section (pre-extraction spiked samples); 2) QCs samples (set 2) prepared using a mixture of de-ionized water:ACN (neat solution). In each set, different ratios of ACN were added (1:1, 1:2 and 1:3). In total, 18 samples were analyzed, 9 samples in each set. The absolute ME was measured by calculating the percentage of the ratio of mean peaks area of pre-extracted samples to samples prepared in de-ionized water/ACN mixture.

Recovery was assessed by analyzing a third set of QCs samples (set 3) prepared by extracting blank OF first with 1:1, 1:2 and 1:3 ACN, followed by adding TAC working standard solutions to achieve required concentrations (post-extraction spiked samples). The recovery was determined by calculating percentage of the ratio of mean peaks area of pre-extraction samples (set 1) to post-extracted spiked samples (set 3).

Results and Discussion

Figure 2:
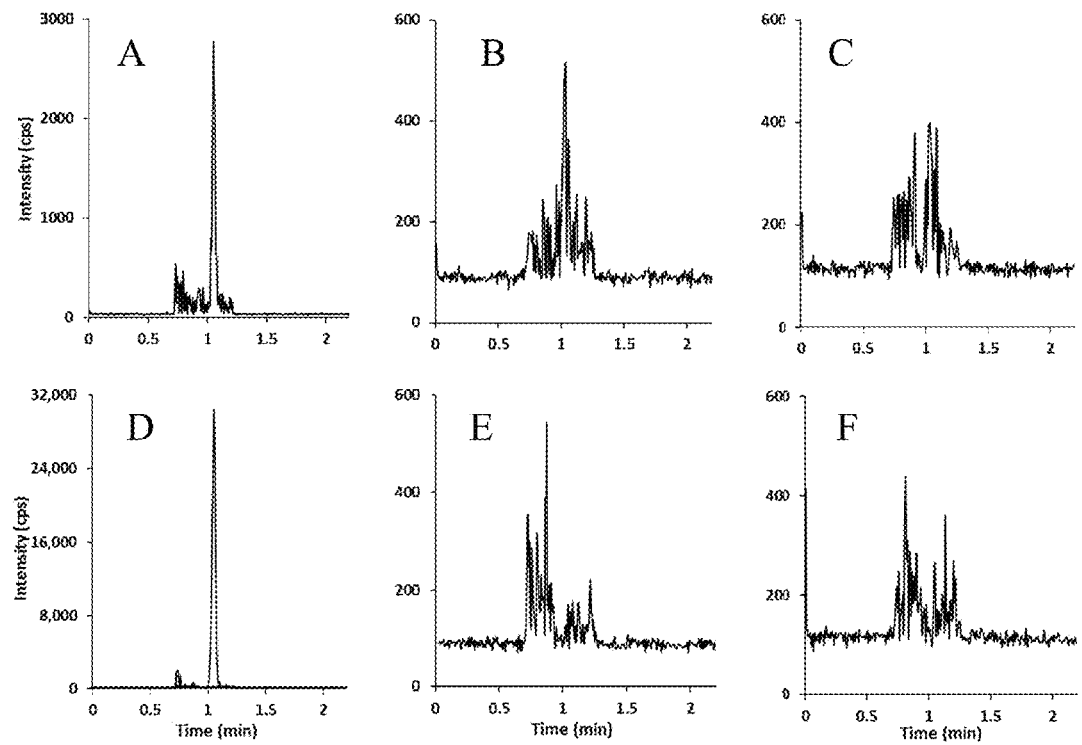
FIG. 2 shows chromatograms of TAC at LLOQ (10 pg/mL) (panel A) and the internal standard ascomycin (400 pg/mL) (panel D,). Chromatograms shown in panel B and panel E show traces of TAC and panels C and F represent a pooled blank OF and a blank solvent samples, respectively, injected immediately after highest calibration curve concentration (1600 pg/mL) injection.

Recommended TAC trough blood concentration (Cmin) in kidney transplant recipients ranges between 15-20 ng/mL immediately after transplantation. TAC dose tapered gradually and maintenance Cmin can be set as low as 5-7 ng/mL after first year post-transplantation. Since only 1% of TAC amount found in unbound form was capable of reaching OF, the expected OF concentration would range from 50-200 pg/mL. Therefore, optimum mass spectrometry and chromatographic conditions were sought in order to develop a method with adequate selectivity and sensitivity. To achieve the highest feasible selectivity, different analytical columns were tested in conjunction with mobile phases of varying composition and gradients. An Acquity UPLC BEH C18 was the best choice as it gave sharp and symmetrical peaks for TAC and IS. Given the above-mentioned UPLC and mass spectrometry conditions, it was possible to set LLOQ at 10 pg/mL with signal/noise ratio more than 10 FIG. 2 (panel A). No carryover was detected when a double blank OF sample was injected following the highest calibration concentration FIG. 2 (panels C and F). The calibration curve was constructed by plotting nominal standard concentrations against peak area ratios of the analyte to IS and fitted with 1/x weighted least squares linear regression. The method demonstrated adequate accuracy and precision with QCs accuracy between 94.5-103.6%, and CV within 4-9.8% (Table 1). The coefficient of determination (R-squared) calculated for validation batches (n=3) was between 0.998-0.999.

Stability studies, namely, freeze and thaw, bench top, auto-sampler, and short-term storage at −80° C. for up to four weeks were conducted (Table 2). TAC was stable in extracted matrix for up to 48 h and no loss of stability was noticed during different stability studies.

Possible interference from endogenous substances in OF was investigated as is represented in chromatograms obtained from a pooled blank OF from six donors (FIG. 2, panel C) and a blank neat solution (66% ACN) (FIG. 2, panel F) were compared. Using the assay conditions described above, no signs of interference were noticed.

Using methanol instead of ACN as an organic solvent improved the sensitivity. Utilization of LC/MS grade methanol showed to increase the sensitivity by approximately 20%. Positive mode ionization and monitoring ammonium adduct [M+NH4]+ at (m/z 821.30→768.35) provided better signal compared to [M]+ and [M+Na]+.

Matrix Effect and Recovery

Co-eluting of drug with endogenous substance in OF may lead to either ion suppression or enhancement, which is collectively called ME. Presence of ME could compromise the reproducibility and may lead to bias in the analysis. Different cleaning procedures were used in other methods that aimed to measure the concentration of immunosuppressive agents in OF. These techniques included solid phase extraction, analyte concentration by drying and reconstituting and simple protein precipitation using organic solvents. Type and percentage of precipitating solution could influence sensitivity and selectivity through its effect on the yield of the analytes and cleanness of the extracted sample. Acetonitrile has been reported to provide satisfactory protein precipitation in oral fluid samples. Recovery of a number of drugs and ME achieved using MeOH and ACN as precipitating solvent in plasma are comparable. However, MeOH tends to retain about 40% more phospholipid. Therefore, ACN was chosen as the extracting solvent. To the best of our knowledge, no other study investigated optimal proportion of extracting solvent (ACN) that gives maximum recovery and sample cleaning up. To examine the effect of using different proportions of ACN on recovery and absolute ME, OF samples were extracted with an equal, double and triple amount of ACN (Table 3). As it can be seen from Table 3, there was slightly less variability in ion abundance in samples extracted with double volume of ACN compared to other two categories. Standard deviations (SD) were ±7-577, ±4-138 and ±11.5-141.6 for OF extracted with equal, double and 3 times volume ACN, respectively. The recovery ranged between (101.6-112.7), (100.0-113.8), and (113.8-124.3); and ME was within (79.8-93.2), (95.6-116.0) and (100.9-131.3) for 1:1, 1:2 and 1:3 OF:ACN respectively. Based on these values, it is obvious that samples extracted with ACN three times of their volume gave exaggerated recoveries, while the other two groups showed comparable recovery ranges. For ME, the first group showed to have significant ion suppression of about 20% in QC1 samples. Considering variability in the acquired data, adequate sample cleaning and recovery, and minimum sample dilution, two-folds of ACN was chosen as the sample to solvent ratio to ensure optimal protein precipitation.

Figure 3:
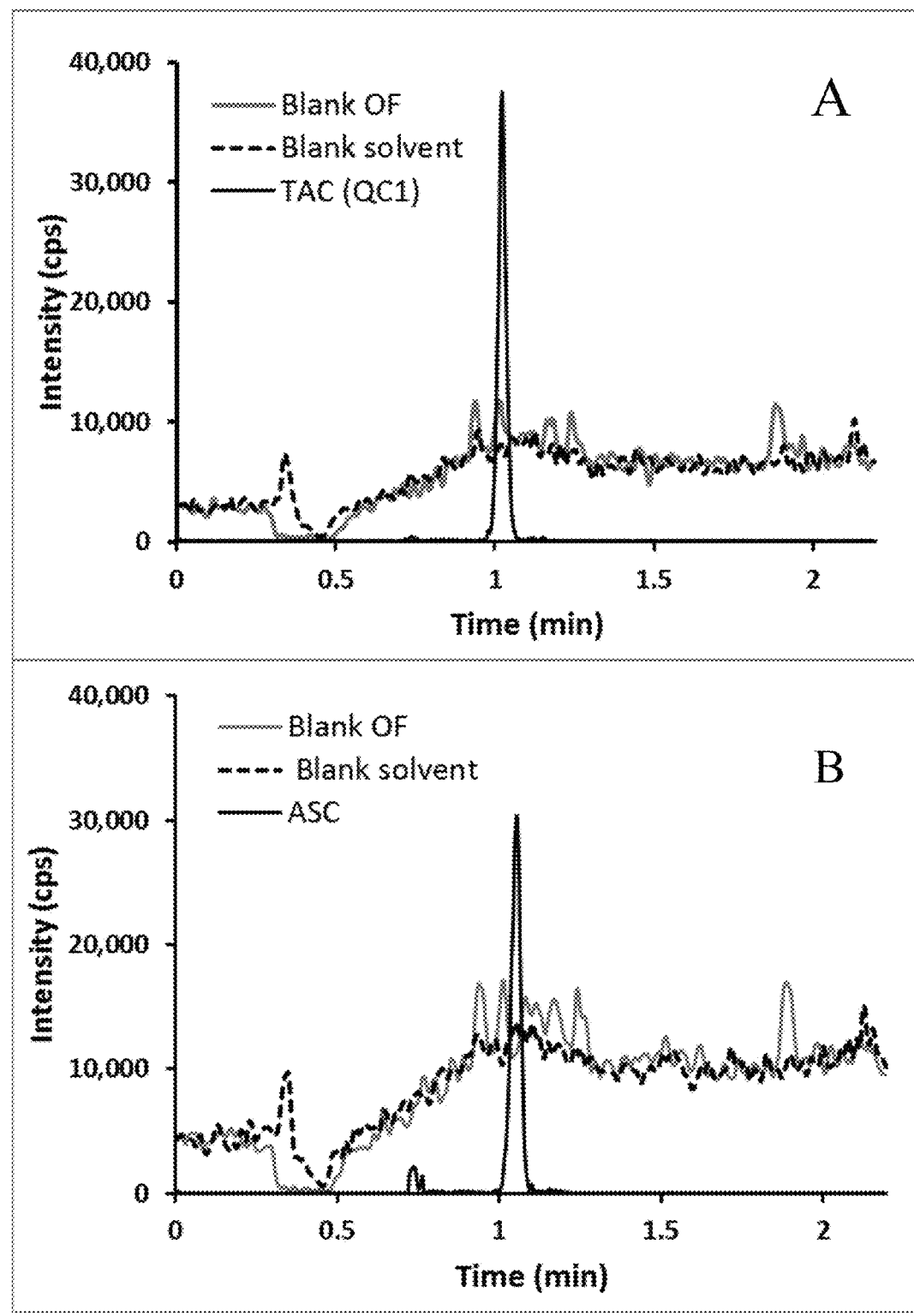
FIG. 3 shows the effect of blank OF and blank solvent injections on chromatograms obtained from continuous post-column infused mixture of TAC and ASC overlaid on TAC at QC2 concentration (400 pg/mL) (panel A) and ASC (panel B).

Matrix effect was explored visually using post-column infusion technique. The composite chromatograms in (FIG. 3, panels A & B) were obtained by overlying chromatograms acquired from injecting a neat solution (66% ACN), a blank OF with continued infusion of a mixture of ASC and TAC (1 ng/mL) and a chromatogram of QC2 injection. The only areas of chromatograms that showed ion suppression are between 0.2-0.5 min, which is far enough from ASC and TAC elution area.

Figure 4:
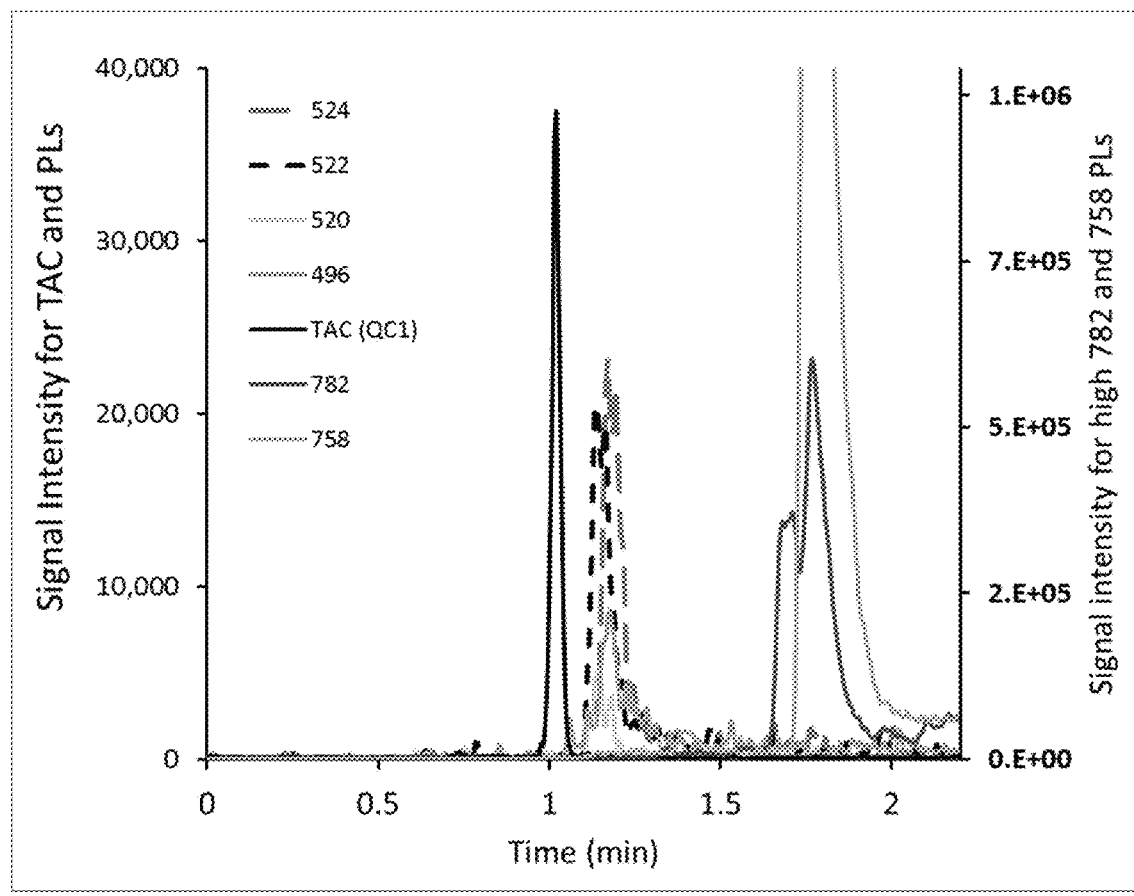
FIG. 4 shows a composite chromatogram showing MRM transitions of six major phospholipids chromatograms obtained from blank OF sample injection overlaid on TAC chromatogram obtained by injecting a pooled OF spiked with TAC at QC2 concentration (panel C).

Finally, potential co-elution of phospholipids was examined by adding MRM of transitions of most common phospholipids to the mass spectrometry method. Phospholipid transitions included were (m/z 496→184, 520→184, 522→084, 524→184, 758→184, 782→084). In early stages of method development, we have observed that ASC and TAC peaks were co-eluting with low molecular weight phospholipids (m/z 496 to 524). The other two phospholipids that have m/z more than 700 were less problematic and eluted long after analytes of interest. As shown in FIG. 4, by manipulating the mobile phase gradient and/or composition, full separation between the analytes of interest and the phospholipids was achieved. To our knowledge, the interference of phospholipids with LC-MS/MS analysis of drugs in OF and resolution of this issue has not been reported previously.

This assay presents an excellent level of sensitivity to enable determination of TAC concentration in OF obtained from stable transplant recipients. In total, out of 181 OF samples analyzed, only one sample had a concentration lower than LLOQ with calculated concentration around 8.5 pg/mL. The concentration of TAC ranged from 11.7-2864.4 pg/mL and 1.7-46.1 ng/mL for OF and whole blood respectively.

Incurred Sample Reanalysis

Figure 5:
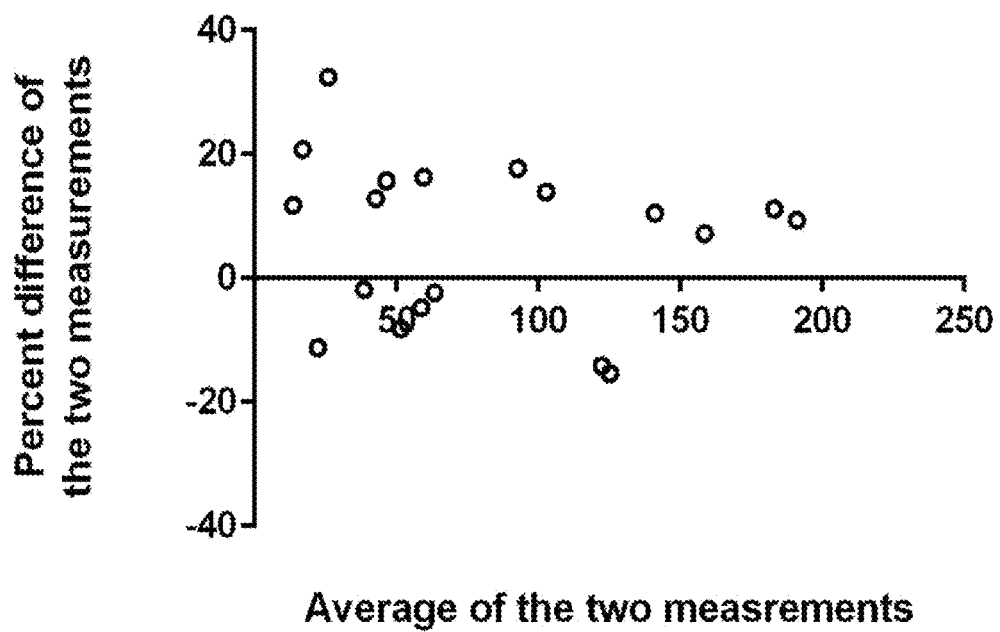
FIG. 5 shows a Bland-Altman plot of the % difference between the repeated measurements plotted against mean differences.

The incurred sample reanalysis test was performed by re-analyzing about 10% of the samples (19 samples). Whenever many samples were available per patient, two samples were selected to represent absorption and elimination phases. The differences between the paired measurements were normally distributed; therefore, the use of Bland-Altman method was justified. Repeatability was tested visually, as shown in FIG. 5, and a statistically good agreement between the two repeated measurements were observed since all points lie between or near the 95% confidence interval limit. The 95% limit of agreement was from −19.16 to +31.98% and the bias (mean difference between two occasions) was 6.40%.

Example 2

For a given drug, the values of area under the concentration-time curve (AUC) and maximum concentration (Cmax) typically correlate better with clinical outcomes and toxicity than a single concentration before dose (trough level). Since AUC calculation requires the collection of several samples over a 12-hour dosing interval, venipuncture blood sampling is not practical for routine calculation of AUC. The simplicity of OF sample collection allows multiple convenient sampling; therefore permitting for easy estimation of AUC and Cmax. The aim of the studies presented in this Example was to determine the factors that influence the concentration of TAC in OF and to lay down the best practices for the collection of OF to assure optimal sample quality and assay performance.

Material and Methods

Study population: Samples included in this study were collected during two clinical studies from stable kidney transplant recipients. Protocol for each clinical study was approved by the Institutional Review Board of Rhode Island Hospital (Providence, R.I.). On the study day, all patients underwent a physical examination by the study physician and were asked to sign an informed consent prior to sample collection. All patients were on a triple immunosuppressant regimen that included tacrolimus, prednisone, and mycophenolic acid. All blood and OF samples were kept on dry ice until transfer to the Clinical Pharmacokinetics Research Laboratory at the University of Rhode Island and subsequent storage at −80° C. until further analysis. Demographic information of the study participants is shown in Table 4.

Study A. Characterization of 12-hour profile of tacrolimus in OFs: The objective of this study was to obtain parallel blood and saliva samples for 12 h after the morning dose tacrolimus. On the morning of the study day, a venous blood sample (about 4 mL) was collected in ethylenediaminetetraacetic acid (EDTA) coated tubes. Simultaneously, OF samples were collected by passive drool (resting) in a siliconized plastic cup. After the administration of morning dose of immunosuppressive agents including tacrolimus, serial samples were collected at certain time points post-dose for 12-hour. All patients fasted overnight but prior to the start of sample collection, took a protein bar with their morning medication together with a glass of water. Thus, the samples obtained in this study was regarded as samples collected at non-fasting state.

Study B. Characterization of the effect of OF sample collection method: Blood samples were collected at pre-dose (C0) and then at two-hour after dose (C2). Patients have arrived at the hospital after an overnight fast and were remained fasted during collection of C0 samples. Matching OF samples were collected within ±5 min from blood sample time by passive drool (resting sample), after mouth rinsing with water (rinsed sample), and immediately after taking a sour candy to stimulate saliva production (stimulated sample). For the following samples, patients were asked to place a small piece of a commercial candy containing citric and tartaric acids (Sour Patch Kids, Mondelēz International, East Hanover, N.J., USA) in their mouth for 10 s with continues tongue movement. After C0 samples collection, patients were given a voucher for breakfast and were asked to report back to the study location shortly before sample collection at two-hour after dose (C2). The same process of blood and corresponding OF sample collection was followed at this time. The C2 samples were regarded as fed state.

Assessment of Saliva Weight, pH and Blood Contamination

Upon thawing saliva samples, an aliquot of saliva was weighed with an analytical balance and the weight was recorded to establish the drug concentration as pg/mg weight. Moreover, the pH of saliva was measured by an Orion STAR A111 pH meter equipped with Micro Electrode from Thermo Scientific (Waltham, Mass., USA). To assess and quantify possible blood contamination of OF, a transferrin kit from Salimetrics LLC (State College, Pa., USA) was used (the validated assay range is ≤6.6 mg/dL). Transferrin (TRNs) is a plasma protein (Mw=76,000) that is used as a biomarker for presence of blood in OF. Transferrin quantification was performed using SpectraMax M5e Microplate Reader (Sunnyvale, Calif., USA).

Measurement of Tacrolimus in Blood and OF

Sample extraction was preformed mixing 200 μL of the blood sample with 800 μL of precipitating solution [ZnSO4 (17.28 g/L) in water and methanol (30:70, v/v) containing 100 ng/mL ascomycin as internal standard]. After vortex mixing, samples were centrifuged for 10 min at 13,000 rpm.

The concentration of tacrolimus in OF was measured using a validated LC-MS/MS method. In brief, chromatography separation was achieved with a run time of 2.2 min using an Acquity UPLC BEH C18 analytical column kept at 60° C. TAC was eluted by gradient elution with 2 mM ammonium acetate/0.1 formic acid in water (mobile phase A) and in methanol (mobile phase B) at 0.4 mL/min flow rate. Initial mobile phase comprised of 50% solvent B, increased gradually to 98% over 0.5 min and maintained at this level until 1.8 min. Then mobile phase was returned to initial conditions within 10 s and maintained until the end of the run at 2.2 min to recondition the column for the next run. The elution time of TAC and internal standard was 1.0 min.

A simple sample preparation and extraction procedure was followed. Briefly, 50 μL of homogenized OF sample was added to 100 μL of ACN precipitating solvent containing internal standard (ascomycin, 600 ng/L). After vortex mixing for 10 s, the mixture was centrifuged at 10,000 g for 5 min at 20° C. The supernatant was then transferred to an auto-sampler vial, and 10 μL was injected onto LC-MS/MS. The dynamic range of the assay was 30-4,800 pg/mL. The lower limit of quantification (LLOQ) was set at the concentration that had a signal-to-noise ratio (S/N) of ≥10; the accuracy of 80-120%; and a coefficient of variation (CV) <20%. The lower limit of quantification (LLOQ) for the assay was set at 10 pg/mL Acceptance criteria for quality controls (QCs) included in the assay was accuracy between 85-115% and CV <15%. Selectivity was assessed by inspecting the presence of noise or peaks in chromatograms blank OF samples injections (from 6 donors) and a comparison with LLOQ chromatogram.

Characterization of Genotype

DNAzol kit was used to extract genomic DNA from blood samples obtained from each patient as described in manufacture's protocol (Invitrogen Corporation, Carlsbad, Calif., USA). Samples were genotyped for SNPs in CYP3A and P-glycoprotein. The genotyping process utilized allelic discrimination with a TaqMan® Drug Metabolism Genotyping assay performed on a Life Technologies 7500 Real-Time PCR system (Life Technologies, Foster City, Calif., USA) Genotyping of CYP3A4, CYP3A5, ABCB1, ABCB11, ABCC2 and ABCG2 genes Genomic DNA from patients' peripheral blood sample was extracted using QIAamp DNA Mini Kit (Qiagen, Valencia, Calif., USA) according to manufacturer's instructions and was stored at −80° C. until analysis. Genetic polymorphism of cytochrome P450 (CYP) 3A4*22 (rs35599367), CYP3A5*3, p-glycoprotein or ABCB1 1236C>T (rs1128503), 2677G>T,A (rs2032582) and 3435C>T (rs1045642), Bile salt export pump (BSEP) or ABCB11 1331C>T (rs2287622), Multidrug resistance-associated protein 2 (MRP2) or ABCC2 −24C>T (rs717620), 1249G>A (rs2273697) and 3972C>T (rs3740066), and Breast cancer resistance protein (BCRP) or ABCG2 421C>A (rs2231142) were determined by TaqMan® allelic discrimination assay (Life Technologies, Foster, Calif., USA) using an Applied Biosystems 7500 Real-Time PCR system (Life Technologies). CYP3A4*1B (rs2740574) was genotyped by PCR amplification and the subsequent direct sequencing using Applied Biosystems 3130xl Genetic Analyzer (Life Technologies, Foster City, Calif., USA). The primers for the amplification of CYP3A4 gene and assignment of ABCC2 haplotypes were described previously.

Statistical Data Analysis

Statistical analysis was performed using the GraphPad Prism version 5 (GraphPad Software Inc., San Diego, Calif., USA) and SPSS software (IBM SPSS, Armonk, N.Y., USA). Normal distribution of the data was checked graphically and confirmed with the Kolmogorov-Smirnov test and nonparametric tests were used whenever applicable. Non-normally distributed data were transformed to natural logarithm, underwent statistical analysis and reported as Geometric mean and 95% confidence interval. To understand the relative importance of various factors influencing the concentration of tacrolimus in OF, analysis of covariance (ANCOVA) was performed on natural log-transformed concentration of tacrolimus in OF. Model discrimination was carried out by estimating reduction in Akaike's Information Criterion (AIC) and inspecting the residual plot for each model.

Results and Discussion

Tacrolimus concentration in OFs and blood. In total, 276 paired OF and blood samples were analyzed. Four OF samples had tacrolimus concentration below 10 pg/mL, the LLOQ for the assay, and four OF samples had concentration above 4800 pg/mL, upper limit of quantification for the assay. These samples were excluded from further analysis. Tacrolimus concentration in blood was 7.4±5 ng/mL (mean±SD) with median value of 5.9 ng/mL. Concentration of tacrolimus in OFs was in OFs was 744±666 pg/mL of homogenized OFs (median 505 pg/mL). The weight of a 50 mL aliquot of homogenized OF was 69±1 mg (median 69 mg). Concentration of tacrolimus corrected for the weight of homogenized OF was 540±485 pg/mg (median 367 pg/mg).

Evidence for blood contamination of OFs by measuring salivary transferrin (TRNs) concentration. About 85% of tacrolimus distribute into red blood cells and high TRNs is an indication of salivary blood contamination that may artificially overestimate drug concentration in OFs. Therefore, the association between TRNs concentration and TAC concentration in OFs in samples collected under different sampling conditions (rested, rinsed and stimulated) was investigated. Four OF samples had TAC concentration higher than upper limit of quantification for the assay and all of them had TRNs level higher than the assay quantification range (0.08-6.6 mg/dL). Four additional samples also had TRNs higher than the upper limit of quantification of 6.6 mg/dL.

12-Hour Profile of Tacrolimus in OFs (Study A)

Figure 6:
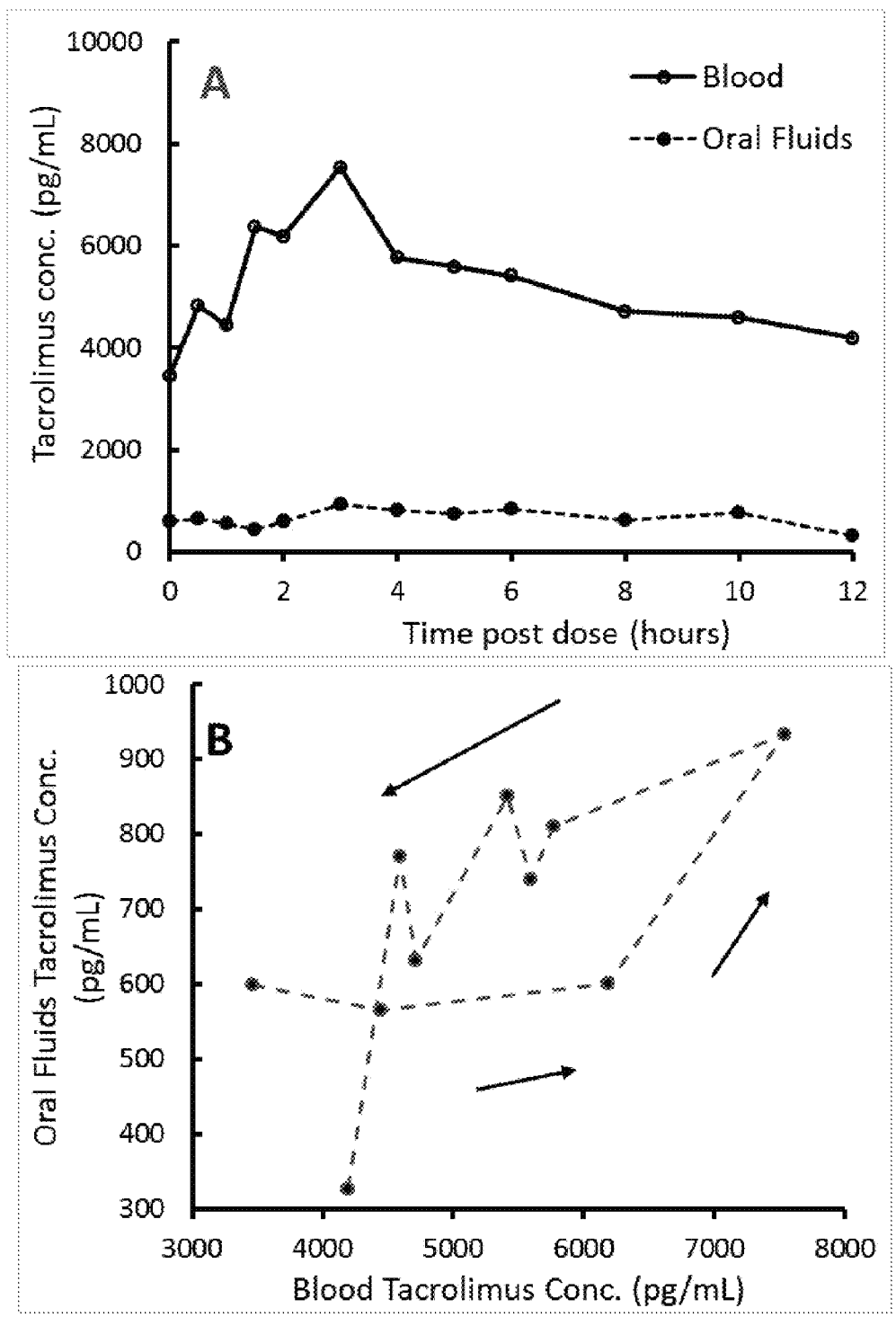
FIG. 6 shows time course data of concentration of tacrolimus in blood and oral fluids over 12-hour dosing interval in 10 stable kidney transplant recipients (panel A) and concentration of tacrolimus in blood versus oral fluids indicating a distributional delay, as evidenced by counter-clockwise hysteresis (panel B).

Eighty paired OF and blood samples collected from 10 patients by passive drool in fed state. The concentration of TAC in blood and oral fluids were 5.7±2.6 ng/mL and 885±650 pg/mL, respectively. Table 5 summarizes the concentration of TAC in blood and OF as well as OF pH and transferrin levels. Because feeding require some degree of mouth rinsing naturally stimulate salivary flow, little evidence of blood contamination was present in samples collected in this study (Table 5). Moreover, saliva pH was relatively constant during the study period. FIG. 6 (panels A & B) depict the average concentration of tacrolimus in blood and OFs over a 12-hour dosing interval (panel A) and tacrolimus concentration in blood versus OFs (panel B). Specifically, FIG. 6 (panel B) shows evidence of counter-clockwise hysteresis or lateness in the concentration of tacrolimus in OF and this hysteresis resemble a distributional delay. In pharmacodynamics, a counter-clockwise hysteresis is generally an indication of a distribution phase, possibly due to redistribution of drug from the vascular compartment to the drug's site of action. Previously it was reported that salivary concentration of procainamide mirrored the time-course of drug at the site of action, cardiac tissue; however, drug concentration in saliva did not parallel plasma concentration and the relationship between plasma and saliva concentration resembled a counter-clockwise hysteresis loop.

Sampling Conditions (Study B)

The objective of the effect of fasting versus fed on the concentration of tacrolimus in oral fluid was investigated. Moreover, the effect of different sampling conditions (resting, mouth rinsing, OF stimulation) on the concentration of tacrolimus in OFs at trough and 2-hour post-dose (C2) was investigated. Changing salivary flow rate may alter drug concentration in the OF via altering contact time and pH thus affecting tubular reabsorption and secretion. Changes of OF flow rate may affect some drugs but have little to no effect on others. Table 6 summarizes the concentration of tacrolimus in OFs with blood concentration, saliva pH and transferrin concentration. First, fasting samples at trough (C0 resting) had an unacceptably high level of blood contamination. Salivary blood contamination may increase in the presence of micro injuries from poor oral hygiene, some infectious diseases and smoking. The presence of TRN in OF is an indication of injury in the oral cavity and based on our findings is exacerbated in fasting C0 samples of OFs obtained without mouth rinsing. Rinsing has improved the problem with blood contamination to some extent but did not resolve it completely.

Significantly lower TAC levels are seen in stimulated OF samples in both pre and 2 hours after dose samples. Lower OF tacrolimus levels are seen in samples collected five minutes after mouth rinsing, but the differences were not statistically significant. Stimulation produced a remarkably larger amount of OF in a short time compared to resting samples and significantly lowered pH of the OF. Based on the drastically lower ratio of tacrolimus in OF to blood in stimulated samples (Table 6) it can be concluded that the method of stimulation used in this study did not produce a desirable stimulating effect.

Establishing a Cut-Off Value for TRNs Concentration in OF

Figure 7:
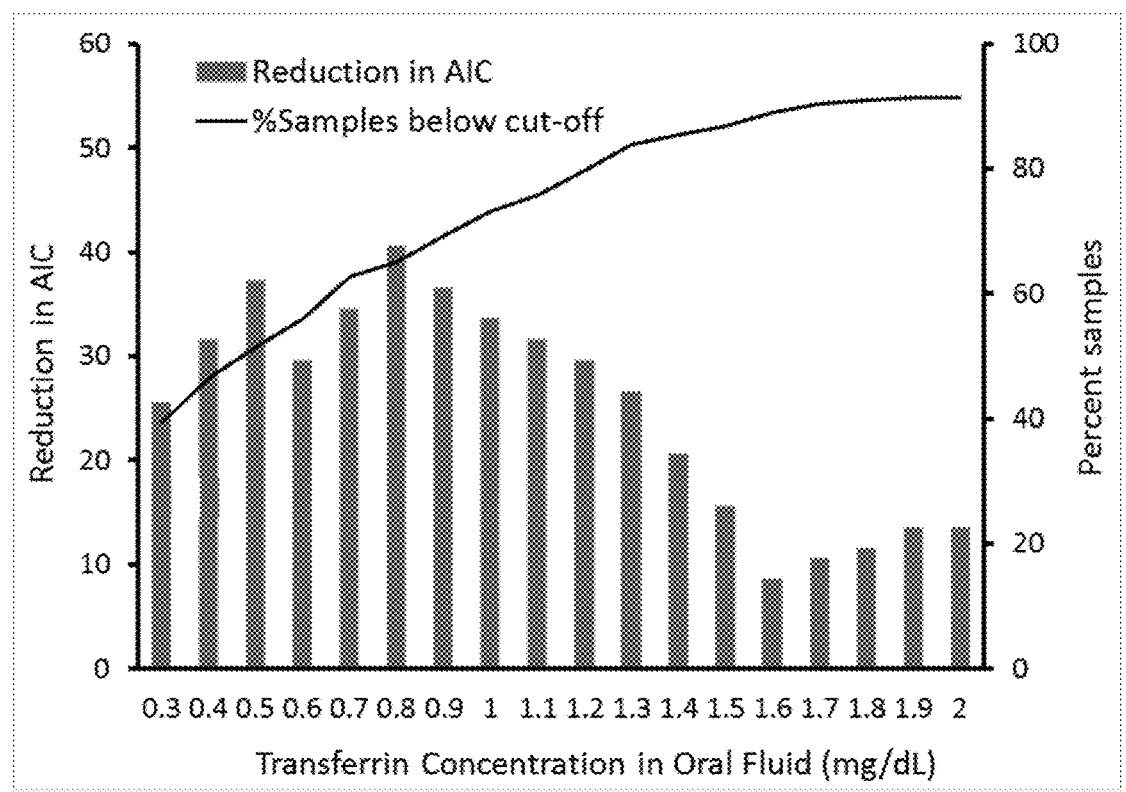
FIG. 7 shows a histogram presenting salivary transferrin concentration data showing reduction in the value of Akaike's Information Criterion (AIC) for an Analysis of Covariance model with respect to cut-off value for salivary transferrin concentration and percentage of non-stimulated oral fluid samples having salivary transferrin level below the cut-off value.

Most saliva-based methods of drug or hormone analysis exclude samples with blood contamination. Thus, the goal was to establish a cut-off value for TRNs level that affects the concentration of tacrolimus present in the OF. All stimulated samples (from Study B) were excluded from this analysis because such samples appeared to be diluted by a higher flow of saliva. An ANCOVA model was used with the concentration of tacrolimus in OF as independent variable and the concentration of tacrolimus in blood as well as TRNs as dependent variables. Samples were groups according to a TRNs level of >0.3 up to >2 mg/dL in 0.1 mg/dL increments. Reduction in AIC was determined as a measure of goodness of fit for each cut-off value and change in AIC was plotted against the cut-off value. As shown in FIG. 7, a TRNs cut-off value of above 1 mg/dL appears to be optimal regarding the reduction in AIC and number of valid samples present among resting and rinsed samples.

Correlation Between Tacrolimus Concentration in OF and Blood

Figure 8:
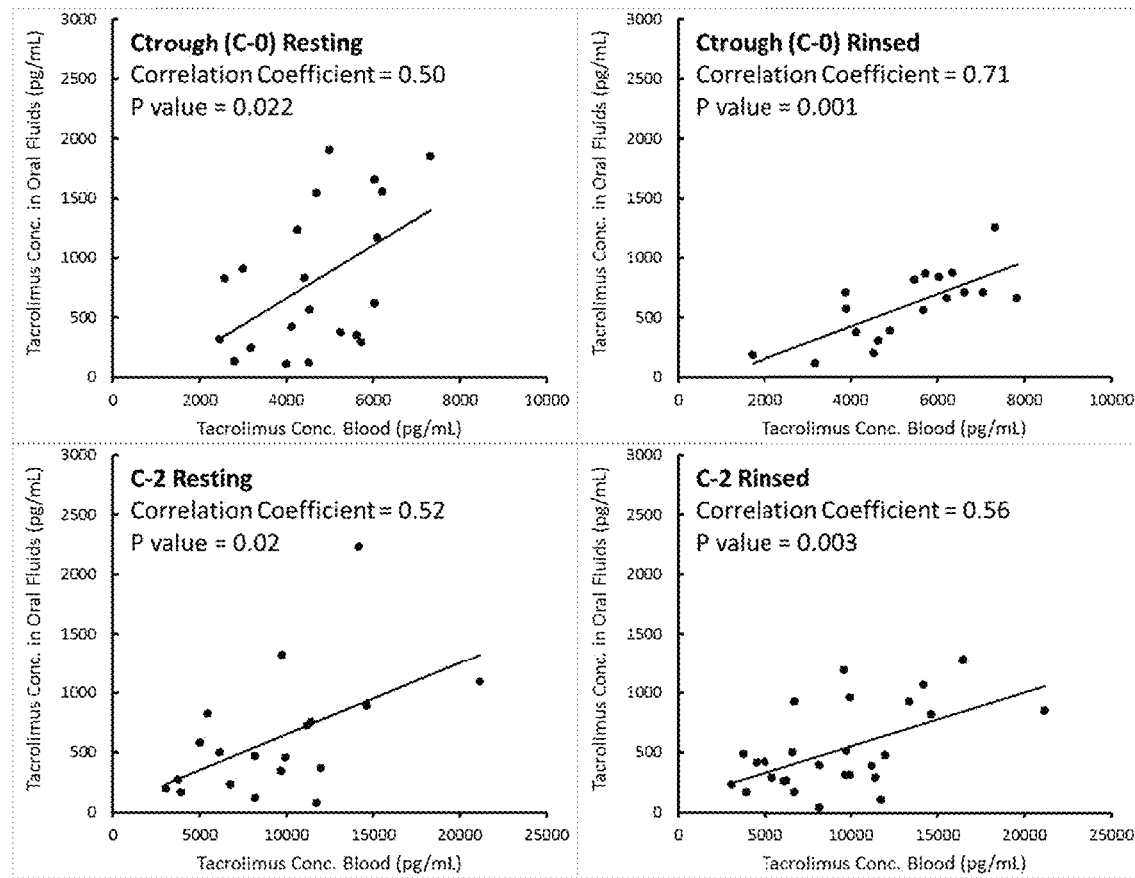
FIG. 8 shows scatter plots showing the association between tacrolimus concentration in blood and oral at trough concentration (C0) or near peak concentration (C2) under resting or rinsed condition. Oral fluids with transferrin concentration greater than 1.0 mg/dL were excluded.
Figure 9:
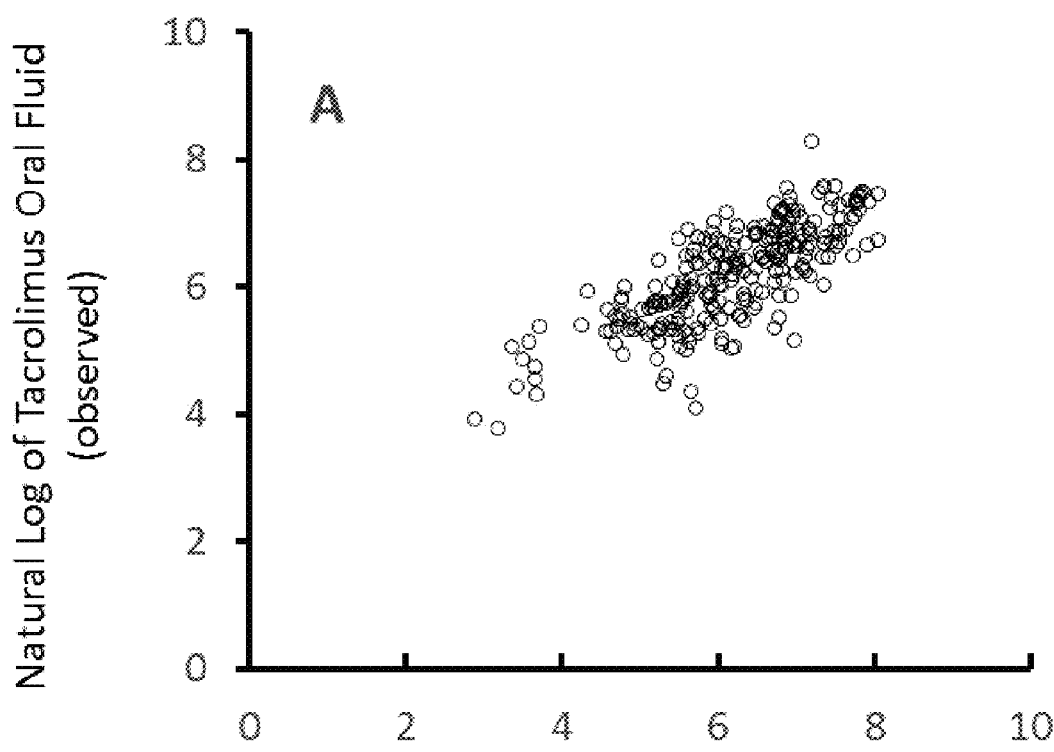
FIG. 9 shows model validation graphs for final ANCOVA model predicting the concentration of tacrolimus in oral fluids (panel A) observed versus predicted concentrations (panel B) predicted concentration versus residuals indicated lack of bias in prediction of tacrolimus OF concentrations by the final model.
Figure 9:
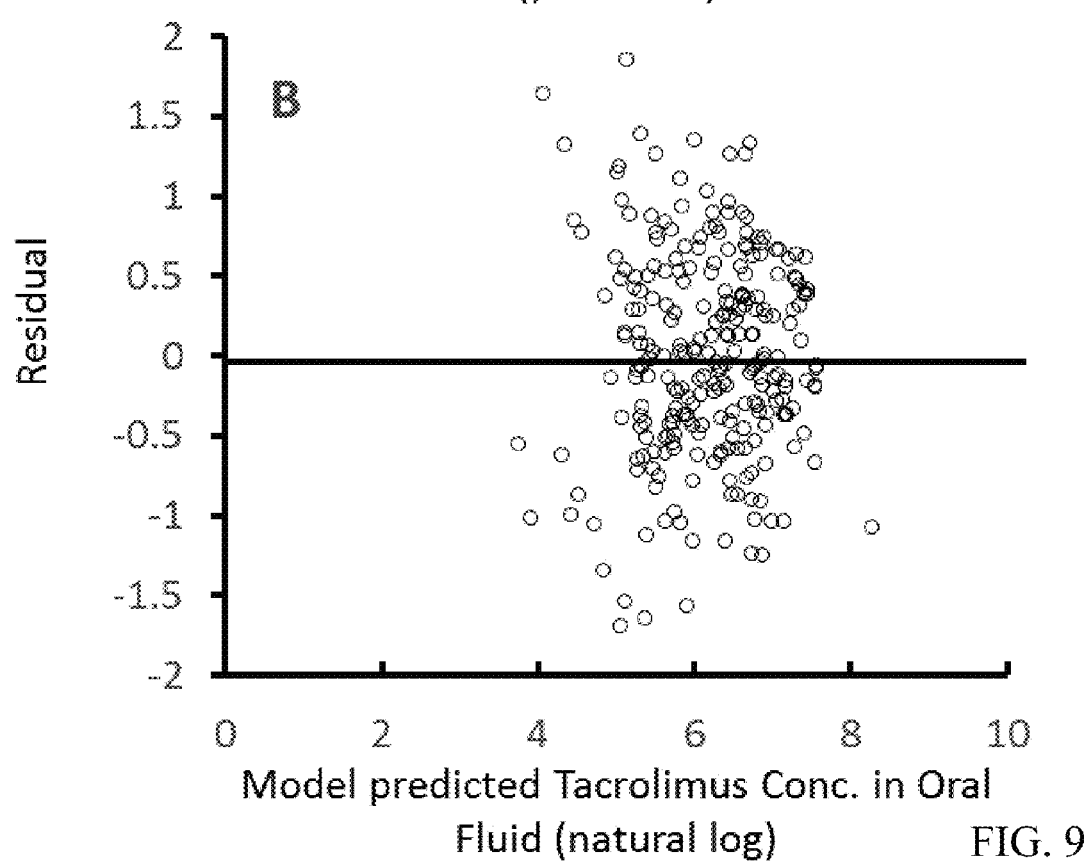

Rinsing of the oral cavity with water lowered blood contamination of OFs (Table 6) and the correlation coefficient between blood and OF concentrations was better than non-rinsed (resting) samples. FIG. 8 shows the association between concentrations of tacrolimus in blood and OF at trough and C2 under resting or rinsed conditions (TRNs level greater than 1 mg/dL was excluded). It appears that rinsing the oral cavity provided the best condition for collection of OF samples.

Multivariate Analysis of Factors Influencing the Concentration of Tacrolimus in OFs To understand which factors influence the concentration of tacrolimus in OFs, an ANCOVA analysis was performed with tacrolimus concentration in OF as the independent variable and tacrolimus blood, sampling condition and time after dose as dependent variables. Then, in a univariate fashion, the effect of demographic characteristics (age, gender, race, ethnicity, and diabetes status), factor related to OF (pH or weight of OF and well as transferrin concentration), biochemical indices (albumin, bilirubin, liver function tests, and total cholesterol) and genetic polymorphisms important for tacrolimus disposition were investigated. Each covariate was added individually and the reduction in AIC value was noted. TRNs was the most significant covariate followed by ABCB11 gene polymorphism (encoding BSEP), serum albumin, bilirubin, total cholesterol, diabetes status, ABCC2 haplotype, SLCO1B1 521, CYP3A5*1 and Gender. Sequential addition of covariates to the base model resulted in loss of significance for some covariates. Factors included in the final model are summarized in Table 7 indicating a strong association between serum albumin, bilirubin and cholesterol concentration and the concentration of tacrolimus in OF. Tacrolimus is highly bound in blood and plasma mainly to red blood cells, albumin and lipoproteins. The result of our study confirms that concentration of tacrolimus in OF is a reflection of the extent of binding in blood or plasma. Thus, tacrolimus concentration in OFs may correlate to a greater extent with drug concentration at the site of action and will be more relevant to measure than blood concentration of tacrolimus.

Several reports were published previously on the concentration of immunosuppressive agents namely, cyclosporine, mycophenolic acid, and TAC in OFs. The single report on the association between tacrolimus concentration in OF and blood performed a simple correlation analysis and concluded that tacrolimus concentration in OF is not a good indication of blood concentration. However, theoretically drug concentration in OFs should not directly correlate with blood or plasma concentration since salivary concentration is a representative of free or unbound rather than total drug. A previous study in liver transplant recipients showed that unbound tacrolimus concentration is well-correlated with the incidence of allograft rejection. Moreover, we have previously shown that cyclosporine unbound fraction is a predictor or heart allograft rejection. The result of the current study suggest that tacrolimus concentration in OF can be a better representation of drug concentration at the site of action and thus it should be further explored as a mean of monitoring the pharmacologically active drug form.

Metabolizing enzymes CYP3A4 and P-gp transporter are expressed in minor and major salivary glands. The possible effect of genetic polymorphism in CYPA3 enzymes and P-gp on the association between TAC concentration in OF and blood was examined. Nonetheless, no statistically significant differences were seen in sample collected with respect to polymorphisms previously reported as a predictor for tacrolimus dose-blood concentration relationship. Surprisingly genetic polymorphism of BSEP (ABCB11 1331 C/T) strongly predicted the concentration of tacrolimus in OF. BSEP that is also regarded as sister P-gp, is an efflux transporter and is a very important mechanism for excretion of xenobiotic and bile acid from hepatocyte into the bile duct. ABCB11 1331 C/T is a very common polymorphism of BSEP that is usually associated with drug-induced cholestasis. An important side effect of tacrolimus is cholestasis. Currently, it is not known if tacrolimus is a substrate for BSEP. However, BSEP is expressed in the salivary gland with an expression level half of that in the liver. Therefore, it will be warranted to investigate the concentration of tacrolimus in relationship to BSEP expression and activity and determine if tacrolimus-induced cholestasis can be diagnosed by measuring tacrolimus concentration in OFs.

Although the disclosure has been described with reference to preferred embodiments, persons skilled in the art will recognize that changes may be made in form and detail without departing from the spirit and scope of the disclosed apparatus, systems and methods.

TABLE 1

Summary of accuracy and precision data obtained from quality control (QC) samples from three individual runs (mean ± % CV, each QC had 6 replicates in each validation run, Total = 18).

|  | LLOQ | QC1 | QC2 | QC3 |
|---|---|---|---|---|
| Quality control samples (pg/mL) | 10 | 30 | 200 | 1200 |
| Accuracy (%) | 103.6 | 103.0 | 94.5 | 99.4 |
| Precision (%) | 9.8 | 6.1 | 5.9 | 4.0 |

Accuracy = (mean concentration/nominal concentration) × 100
Precision expressed as % CV = (standard deviation/mean) × 100.

TABLE 2

Result of stability studies (mean ± % CV, N = 3).

| QC concentration | Bench top | Freeze & thaw | Auto-sampler 24 hrs | Auto-sampler 48 hrs | Short-term 1 weeks | Short-term 4 weeks |
|---|---|---|---|---|---|---|
| QC1 (30 pg/mL) |  |  |  |  |  |  |
| % Accuracy (% CV-) | 111.1 (9.4) | 108.2 (5.8) | 105.3 (9.6) | 102.5 (4.3) | 98.4 (11.9) | 100.8 (6.7) |
| QC3 (1200 pg/mL) |  |  |  |  |  |  |
| % Accuracy (% CV) | 98.8 (2.4) | 111.9 (2.0) | 102.2 (2.7) | 105.6 (3.6) | 98.9 (3.4) | 102.9 (1.9) |

TABLE 3

Effect of different ratios of oral fluid sample: extraction solvent (ACN) on recovery and absolute matrix effect, expressed as mean peak area ± SD (n = 3).

|  | QC1 (30 pg/mL) | | | QC2 (200 pg/mL) | | | QC3 (1200 pg/mL) | | |
|---|---|---|---|---|---|---|---|---|---|
| Matrix | 1:1 | 1:2 | 1:3 | 1:1 | 1:2 | 1:3 | 1:1 | 1:2 | 1:3 |
| De-ionized water | 104 ± 8 | 92 ± 4 | 85 ± 15 | 1592 ± 45 | 1739 ± 50 | 1719 ± 142 | 4260 ± 577 | 4653 ± 109 | 4409 ± 138 |
| Extracted OF | 83 ± 7 | 106 ± 8 | 112 ± 14 | 1485 ± 139 | 1689 ± 54 | 1775 ± 47 | 3916 ± 139 | 4452 ± 139 | 4452 ± 63 |
| Post-extraction Spiked OF | 82 ± 8 | 106 ± 6 | 96 ± 12 | 1317 ± 36 | 1484 ± 67 | 1559 ± 67 | 3760 ± 245 | 4090 ± 20 | 3579 ± 59 |
| Recovery(%) | 101.6 | 100.0 | 116.3 | 112.7 | 113.8 | 113.8 | 104.1 | 108.8 | 124.3 |

TABLE 4

Summary of demographic characteristics of the kidney transplant recipients participated in the study

| Gender (M/F) | 26/19 |  |
|---|---|---|
| Diabetes status (ND/D) | 19/26 |  |
|  | Mean ± SD | Range |
| Age (years) | 50 ± 13 | 21-74 |
| Body surface area (m$^2$) | 2.0 ± 0.3 | 1.4-2.4 |
| Tacrolimus dose (mg/day) | 3.9 ± 2.8 | 0.5-12.0 |
| Tacrolimus morning dose (mg) | 2.3 ± 1.4 | 0.5-6.0 |
| Albumin (g/dl) | 4.3 ± 0.3 | 3.3-4.8 |
| Total cholesterol (mg/dl) | 180 ± 36 | 115-268 |
| HDL (mg/dl) | 48 ± 13 | 20-72 |
| Triglycerides (mg/dl) | 170 ± 113 | 50-625 |
| Uric acid (mg/dl) | 6.3 ± 1.6 | 3.9-10.7 |
| Creatinine clearance (ml/min) | 86 ± 27 | 54-168 |
| Bilirubin (mg/dL) | 0.42 ± 0.20 | 0.20-1.30 |
| AST (IU/L) | 31 ± 48 | 9-333 |
| ALT (IU/L) | 24 ± 18 | 8-93 |
| Sodium (mmol/L) | 140 ± 3 | 133-145 |
| CO2 mmol/L | 21 ± 3 | 13-26 |
| Chloride (mmol/L) | 103 ± 3 | 95-109 |
| Glycated hemoglobin (%) | 7.4 ± 1.9 | 4.4-11.7 |

TABLE 5

Geometric mean and 95% confidence interval of tacrolimus concentration in blood and oral fluid (OF), PF to blood concentration ratio*100, pH and transferrin concentration obtained over a 12-hour post-dose

|  | Tacrolimus Conc. in OF (pg/mL) | Tacrolimus blood Conc. (ng/mL) | OF/blood Conc. (*100) | pH of oral fluid | Transferrin Conc. (mg/dL) |
|---|---|---|---|---|---|
| Trough (C0)# | 430 (272, 680) | 3.8 (3.1, 4.7) | 11 (7, 18) | 7.4 (7.1, 7.7) | 0.3 (0.1, 0.5) |

TABLE 5-continued

Geometric mean and 95% confidence interval of tacrolimus concentration in blood and oral fluid (OF), PF to blood concentration ratio*100, pH and transferrin concentration obtained over a 12-hour post-dose

| | Tacrolimus Conc. in OF (pg/mL) | Tacrolimus blood Conc. (ng/mL) | OF/blood Conc. (*100) | pH of oral fluid | Transferrin Conc. (mg/dL) |
|---|---|---|---|---|---|
| Peak (C2) | 573 (411, 599) | 5.5 (4.6, 6.5) | 11 (7, 16) | 7.3 (7.0, 7.6) | 0.2 (0.1, 0.4) |
| All other times | 783 (627, 878) | 5.5 (5.0, 5.9) | 14 (11, 16) | 7.4 (7.3, 7.5) | 0.3 (0.2, 0.3) |

Trough (C0) concentration included levels obtained at morning trough (C0) or evening trough (C12)

TABLE 6

Geometric mean and 95% confidence interval of tacrolimus concentration in blood and oral fluid (OF), PF to blood concentration ratio * 100, pH and transferrin concentration obtained under different condition of oral fluids

| Sampling time | Sampling Condition | Tacrolimus Conc. in OF (pg/mL) | Tacrolimus blood Conc. (ng/mL) | OF/blood Conc. (*100) | pH of oral fluid | Transferrin Conc. (mg/dL) |
|---|---|---|---|---|---|---|
| C0 (fasted) | Resting | 1003 (747, 1348) | 5.5 (4.7, 6.3) | 19 (14, 24) | 7.4 (7.1, 7.6) | 1.4 (1.0, 2.2) |
| | Rinsed | 584 (436, 782) | 5.4 (4.7, 6.3) | 11 (9, 13) | 7.6 (7.4, 7.8) | 0.8 (0.5, 1.2) |
| | Stimulated | 164 (119, 226) | 5.5 (4.8, 6.2) | 3 (2, 4) | 4.6 (4.2, 5.0) | 0.2 (0.1, 0.4) |
| C2 (fed) | Resting | 635 (437, 923) | 9.4 (7.6, 11.7) | 7 (5, 9) | 7.1 (6.9, 7.3) | 0.4 (0.3, 0.6) |
| | Rinsed | 468 (347, 630) | 9.0 (7.4, 11.0) | 5 (4, 7) | 7.4 (7.2, 7.6) | 0.3 (0.2, 0.4) |
| | Stimulated | 235 (167, 330) | 8.8 (7.6, 10.2) | 3 (2, 4) | 4.4 (4.0, 4.7) | 0.2 (0.1, 0.3) |

TABLE 7

Final Analysis of Covariance (ANCOVA) model comprising of factors predicting the concentration of tacrolimus in oral fluids (OFs). The results clearly shows that factors predicting the concentration of tacrolimus in OF are mostly related to the binding of tacrolimus in blood/plasma and an indirect evidence that by measuring the concentration of tacrolimus in OF, we are actually measuring the free or pharmacologically form of tacrolimus. Dependent variable: tacrolimus concentration in OF (natural log transformed)

| Parameter | B | Std. Error | Wald Chi-Square | df | P value |
|---|---|---|---|---|---|
| (Intercept) | 1.592 | 1.144 | 1.936 | 1 | 0.16 |
| Tacrolimus blood concentration (natural log transformed) | 0.395 | 0.098 | 16.37 | 1 | $5.21*10^{-05}$ |
| Time post-dose | | | | | |
| Ctrough (C0) | -0.281 | 0.135 | 4.292 | 1 | $3.83*10^{-02}$ |
| C2 | -0.390 | 0.128 | 9.232 | 1 | $2.38*10^{-03}$ |
| Other times | $0^a$ | | | | |
| Sampling condition | | | | | |
| Resting | 1.338 | 0.111 | 144.3 | 1 | 0.001 |
| Rinsed | 0.947 | 0.116 | 66.96 | 1 | $2.22*10^{-16}$ |
| Stimulated | $0^a$ | | | | |
| Transferrin in OF | | | | | |
| ≤1 mg/dL | -0.584 | 0.102 | 32.52 | 1 | $1.1810*^{-08}$ |
| >1 mg/dL | $0^a$ | | | | |
| Diabetes status | | | | | |
| No | -0.996 | 0.454 | 4.805 | 1 | 0.03 |
| Yes | $0^a$ | | | | |
| BSEP polymorphism | | | | | |
| ABCB11 C/C | 0.348 | 0.125 | 7.695 | 1 | $5.54*^{-03}$ |
| ABCB11 C/T | 0.537 | 0.120 | 20.08 | 1 | $7.44*10^{-06}$ |
| ABCB11 T/T | $0^a$ | | | | |
| Albumin | 0.568 | 0.154 | 13.53 | 1 | $2.35*10^{-04}$ |
| Cholesterol | -0.009 | 0.002 | 34.37 | 1 | $4.56*10^{-09}$ |
| Bilirubin | -0.861 | 0.265 | 10.58 | 1 | $1.14*10^{-03}$ |
| [Diabetes status no] * Cholesterol | 0.008 | 0.003 | 9.696 | 1 | $1.85*10^{-03}$ |
| [Diabetes status yes] * Cholesterol | $0^a$ | | | | |
| (Scale) | $0.410^b$ | 0.036 | | | |

BSEP: Bile Salt Export Pump;
OF: oral fluid;
C0: trough concentration;
C2: tacrolimus concentration at 2-hour post-dose

What is claimed is:

1. A method of measuring tacrolimus in a subject comprising:
   a. collecting oral fluid from the subject;
   b. homogenizing the oral fluid;
   c. combining the homogenized oral fluid with a precipitating solvent;
   d. separating oral fluid components on a liquid chromatography column by gradient elution with a mixture of a solvent A and a solvent B, wherein the solvent A is 2 ammonium acetate and formic acid in water and solvent B is ammonium acetate and formic acid in MeOH and wherein the amount of solvent B is increased from about 50% (v/v) to about 98% (v/v); and
   e. determining amount of tacrolimus in the oral fluid by mass spectrometry.

2. The method of claim 1, wherein solvent A is about 2 mM ammonium acetate/0.1% (v/v) formic acid in water and solvent B is about 2 mM ammonium acetate/0.1% (v/v) formic acid in MeOH.

3. The method of claim 1, wherein solvent B is increased from about 50% (v/v) to about 98% (v/v) over about 30 seconds.

4. The method of claim 2, wherein solvent B is maintained at about 98% (v/v) for about 1.8 minutes.

5. The method of claim 1, further comprising adding an internal standard to the mixture of step (c) and wherein the internal standard is ascomycin.

6. The method of claim 1, wherein the precipitating solvent is acetonitrile.

7. The method of claim 6, wherein the volume of acetonitrile is about double the volume of oral fluid.

8. The method of claim 1 wherein mass spectrometry is performed in multiple reaction monitoring (MRM) mode.

9. The method of claim 8, wherein collision energy is 20, cone voltage is 28, capillary voltage is 1.50 kV, source temperature is 150° C., cone gas flow is 25 L/hr, desolvation gas flow is 1000 L/hr, and collision gas flow is 0.15 mL/min.

10. The method of claim 8, wherein precursors are $[M+NH_4]^+$.

11. The method of claim 1, wherein the liquid chromatography column has a particle size of about 1.7 μm and a pore size of about 130 Å.

12. The method of claim 11, further comprising passing the oral fluid components through a pre-column, prior to passing through the analytic column.

13. The method of claim 1, wherein the step of homogenizing the oral fluid further comprises:
   a. vortexing the oral fluid; and
   b. sonicating the oral fluid.

14. The method of claim 1, wherein the subject has received an organ transplant and wherein the organ transplant is a liver, a kidney or a heart transplant.

15. The method of claim 1, wherein the step of collecting oral fluid from a subject further comprises the step of pre-rinsing the mouth of the subject, prior to oral fluid collection.

16. The method of claim 1, further comprising:
   a. determining the concentration of transferrin in the oral fluid; and
   b. excluding the oral fluid from further analysis if the oral fluid has transferrin concentration outside a pre-defined range.

17. The method of claim 16, wherein the pre-defined range is above about 1 mg/dL.

18. The method of claim 1, wherein the amount of tacrolimus determined in step (e) is a measure of pharmacologically active tacrolimus in the subject.

19. A method of adjusting tacrolimus dosage for an organ transplant patient comprising:
   a. collecting an oral fluid sample from the patient;
   b. homogenizing the oral fluid;
   c. combining the homogenized oral fluid with a precipitating solvent; and
   d. separating oral fluid components on a liquid chromatography column by gradient elution with a mixture of a solvent A and a solvent B, wherein the solvent A is about 2 mM ammonium acetate/0.1% (v/v) formic acid in water and solvent B is about 2 mM ammonium acetate/0.1% (v/v) formic acid in MeOH and wherein the amount of solvent B is increased from about 50% (v/v) to about 98% (v/v); and
   e. determining the concentration of tacrolimus in the oral fluid by mass spectrometry; wherein an oral fluid concentration of tacrolimus above 200 ng/L indicates a need to decrease tacrolimus dosage and an oral fluid concentration of tacrolimus below 5 ng/L indicates a need to increase tacrolimus dosage.

20. A kit for measuring tacrolimus in a subject comprising:
   a. a vessel for collecting oral fluid from the subject;
   b. a homogenization buffer comprising a precipitating solvent;
   c. one or more liquid chromatography columns;
   d. a first elution buffer comprising about 2 mM ammonium acetate/0.1% (v/v) formic acid in water;
   e. a second elution buffer comprising about 2 mM ammonium acetate/0.1% (v/v) formic acid in MeOH; and
   f. an internal standard sample.

* * * * *